US012589085B2

(12) United States Patent
Peng

(10) Patent No.: US 12,589,085 B2
(45) **Date of Patent: *Mar. 31, 2026**

(54) USE OF DIAMINOGUANIDINE DERIVATIVE AND FEED COMPOSITION THEREOF IN PREPARATION OF VETERINARY DRUG

(71) Applicant: GUANGZHOU INSIGHTER BIOTECHNOLOGY CO., LTD, Guangzhou (CN)

(72) Inventor: Xianfeng Peng, Guangzhou (CN)

(73) Assignee: Guangzhou Insighter Biotechnology Co., Ltd., Guangzhou (CN)

( * ) Notice: Subject to any disclaimer, the term of this patent is extended or adjusted under 35 U.S.C. 154(b) by 1054 days.

This patent is subject to a terminal disclaimer.

(21) Appl. No.: 17/627,133

(22) PCT Filed: Jul. 22, 2019

(86) PCT No.: PCT/CN2019/096997

§ 371 (c)(1),
(2) Date: Jan. 14, 2022

(87) PCT Pub. No.: WO2021/012138

PCT Pub. Date: Jan. 28, 2021

(65) Prior Publication Data

US 2022/0287991 A1 Sep. 15, 2022

(51) Int. Cl.

| | |
|---|---|
| ***A61K 31/155*** | (2006.01) |
| ***A61K 31/24*** | (2006.01) |
| ***A61P 15/00*** | (2006.01) |
| ***A61P 17/00*** | (2006.01) |
| ***A61P 31/04*** | (2006.01) |

(52) U.S. Cl.

CPC ............ *A61K 31/155* (2013.01); *A61K 31/24* (2013.01); *A61P 15/00* (2018.01); *A61P 17/00* (2018.01); *A61P 31/04* (2018.01)

(58) Field of Classification Search

CPC .......... A61K 31/155; A61P 7/00; A61P 31/04; A61P 15/00

See application file for complete search history.

(56) References Cited

U.S. PATENT DOCUMENTS

| | | | | |
|---|---|---|---|---|
| 9,663,458 | B2 * | 5/2017 | Peng | A61P 3/00 |
| 10,253,002 | B2 * | 4/2019 | Page | C07D 333/58 |
| 10,370,341 | B2 | 8/2019 | Page et al. | |
| 11,116,735 | B2 | 9/2021 | Peng et al. | |
| 2017/0342026 | A1 | 11/2017 | Peng et al. | |
| 2020/0016099 | A1 | 1/2020 | Peng et al. | |

FOREIGN PATENT DOCUMENTS

| | | | | |
|---|---|---|---|---|
| CN | 103880712 A | 6/2014 | | |
| CN | 104744321 A | 7/2015 | | |
| CN | 105030744 A | 11/2015 | | |
| CN | 105579432 A | 5/2016 | | |
| WO | 2008014266 A2 | 1/2008 | | |
| WO | WO-2014176636 A1 * | 11/2014 | | A01N 43/54 |
| WO | 2016033635 A1 | 10/2016 | | |

OTHER PUBLICATIONS

Examination report 1 from Chinese Patent Office, dated Dec. 9, 2020.
English translation of 105030744A.
English translation of CN104744321A.
English translation of CN103880712A.
English translation of CN105579432A.
International Search Report of PCT/CN2019/096997, dated Mar. 6, 2020.
English Translation of International Search Report of PCT/CN2019/096997.
Pelttari Eila, "Carbohydrazones of Substituted Salicylaldehydes as Potential Lead Compounds for the Development of Narrow-Spectrum Antimicrobials," Verlag der Zeitschrift fur Naturforschung, 62c, 483-486, Jan. 27, 2007 (Jan. 27, 2007).
M. Marien, "In Vitro Activity of Robenidine Hydrochloride on Rabbit Clostridium Perfringensisolates," Pathology and Hygiene, 9th Word Rabbit Congress, Jun. 10-13, 2008 (Jun. 10, 2008-Jun. 13, 2008).
Rebecca J Abraham et al., "Robenidine Analogues as Gram-Positive Antibacterial Agents," J Med Chem, vol. 59, No. 5, pp. 2126-2138, Jan. 14, 2016.

* cited by examiner

*Primary Examiner* — Kevin E Weddington
(74) *Attorney, Agent, or Firm* — Kam Wah Law

(57) ABSTRACT

Disclosed is a use of a diaminoguanidine derivative and a feed composition thereof in the preparation of a veterinary drug. Particularly, disclosed is a use of a diaminoguanidine derivative having a structure of formula (I), or a stereoisomer, geometric isomer, tautomer, solvate, pharmaceutically acceptable salt thereof, or a prodrug thereof, in the preparation of an animal drug for preventing, managing, treating, or alleviating a disease resulting from bacterial infection, wherein R is $NO_2$, or a group represented by formula (II) or formula (III); $R_1$ is a linear or branched $C_1$-$C_{20}$ alkyl group; A is O, NH or S; $R_2$ is a linear or branched $C_3$-$C_{14}$ alkyl, $C_5$-$C_6$ cycloalkyl, $C_5$-$C_6$ aryl or $CH_2(C_5$-$C_6$ aryl) group. The diaminoguanidine derivative is a non-toxic and safe compound for animals, and is markedly effective in the treatment of infectious diseases in the reproductive system, skin, etc., of farmed animals.

11 Claims, No Drawings

USE OF DIAMINOGUANIDINE DERIVATIVE AND FEED COMPOSITION THEREOF IN PREPARATION OF VETERINARY DRUG

CROSS REFERENCE TO RELATED APPLICATION

This is a U.S. national stage application of the International Patent Application No. PCT/CN2019/096997, filed Jul. 22, 2019, which is incorporated herein by reference in its entirety.

FIELD OF THE INVENTION

The invention belongs to the field of pharmaceuticals, and specifically relates to the use of a diaminoguanidine derivative and a pharmaceutical composition thereof in the preparation of a medicament, in particular, for preventing, managing, treating or alleviating a disease caused by bacterial infection in an animal.

BACKGROUND OF THE INVENTION

In the animal farming industry, livestock and poultry often cause an inflammatory disease due to bacterial infections, such as urogenital disease, gastrointestinal disease, respiratory disease, skin infection, and the like, which will seriously affect the production performance and health of livestock and poultry. The commonly used and effective methods are antibacterial agents or hormone therapy to overcome this problem. With the massive use of antibacterial agents, drug-resistant strains continue to increase, and the use of antibacterial agents or hormones inevitably leads to drug residues in animal products, bringing serious harm to human health.

DESCRIPTION OF THE INVENTION

Accordingly, provided herein is a pharmaceutical composition, comprising at least one of a diaminoguanidine derivative, or a stereoisomer, geometric isomer, tautomer, solvate, or pharmaceutically acceptable salt, or a prodrug thereof, and optionally a feed excipient. Also provided herein is use of the pharmaceutical composition and the diaminoguanidine derivative or a stereoisomer, geometric isomer, tautomer, solvate, pharmaceutically acceptable salt, or prodrug thereof in the preparation of a medicament for animal, for the purpose of providing safe and effective anti-infective agents for animals for the current farming industry.

In order to achieve at least one object of this application, the following technical solutions are specially adopted:

In one aspect, provided herein is a diaminoguanidine derivative according to Formula (I), or a stereoisomer, geometric isomer, tautomer, solvate, pharmaceutically acceptable salt, or prodrug.

Formula (I)

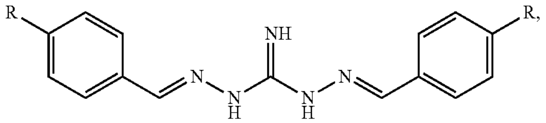

In some embodiments, R is $NO_2$, or R is according to Formula (II) or (III);

Formula (II)

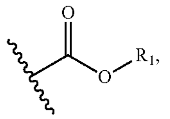

Formula (III)

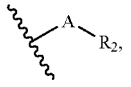

wherein $R_1$ is a linear or branched $C_1$-$C_{20}$ alkyl group; A is O, NH or S; and $R_2$ is a linear or branched $C_3$-$C_{14}$ alkyl group, $C_5$-$C_6$ cycloalkyl, $C_5$-$C_6$ aryl, or —$CH_2$($C_5$-$C_6$ aryl).

In some embodiments, R is according to Formula (II), and $R_1$ is a linear $C_1$-$C_{20}$ alkyl group.

In some embodiments, R is according to Formula (II), and $R_1$ is a linear $C_1$-$C_{12}$ alkyl group.

In some embodiments, R is according to Formula (II), wherein $R_1$ is preferably methyl.

In some embodiments, R is according to Formula (III), wherein A is preferably O.

In some embodiments, R is according to Formula (III), wherein A is preferably NH.

In some embodiments, R is according to Formula (III), wherein $R_2$ is a linear $C_3$-$C_{14}$ alkyl group.

In some embodiments, R is according to Formula (III), wherein $R_2$ is a branched $C_3$-$C_{14}$ alkyl group.

In some embodiments, R is according to Formula (III), wherein $R_2$ is preferably a branched $C_3$ alkyl group or a branched $C_4$ alkyl group.

In some embodiments, the pharmaceutically acceptable salt of the diaminoguanidine derivative is a D,L-lactic acid salt, methanesulfonic acid salt, 2-hydroxyethyl sulfonic acid salt, citric acid salt, tartaric acid salt, benzoic acid salt, succinic acid salt, fumaric acid salt, maleic acid salt, acetic acid salt, sulfuric acid salt, phosphoric acid salt, or oxalic acid salt.

In another aspect, provided herein is a pharmaceutical composition comprising at least one of the diaminoguanidine derivative according to Formula (I), or a stereoisomer, geometric isomer, tautomer, solvent, a pharmaceutically acceptable salt, or prodrug, and optionally a pharmaceutically acceptable excipient.

In some embodiments, the pharmaceutical composition further comprises one or more therapeutic agents.

In some embodiments, provided herein is a diaminoguanidine derivative according to Formula (I), or a stereoisomer, geometric isomer, tautomer, solvate, pharmaceutically acceptable salt, or prodrug thereof, and a pharmaceutical composition thereof in the preparation of a medicament for animal.

In some embodiments, the medicament is useful for preventing a disease caused by bacterial infection.

In some embodiments, the medicament is useful for treating a disease caused by bacterial infection.

In some embodiments, the medicament is useful for alleviating a symptom of a disease caused by bacterial infection.

In another aspect, also provided herein is a method for preventing, managing, treating, or alleviating a disease caused by bacterial infection, and the method is based on a medicament prepared with the diaminoguanidine derivative according to Formula (I) or a stereoisomer, geometric isomer, tautomer, solvate, pharmaceutically acceptable salt, or prodrug thereof, and a pharmaceutical composition thereof to inhibit the growth of bacteria.

The beneficial effects provided herein are:

The diaminoguanidine derivative provided herein is a non-toxic and safe compound for animals, and has significant efficacy for the treatment of an infectious disease in the reproductive system, skin, and the like of a farmed animal.

Any one embodiments of any aspect provided herein can be combined with other embodiments as long as there is no contradiction between them. In addition, in any one of embodiments of any aspect provided herein, any one of technical features can be suitable for that technical feature in other embodiments, as long as there is no contradiction between them.

DESCRIPTION OF EXEMPLARY EMBODIMENTS

The foregoing described herein only outlines certain aspects of this application, but is not limited to these aspects. The above-mentioned aspects and other aspects will be described in more detail and complete below.

DETAILED DESCRIPTION OF THE INVENTION

Now certain embodiments provided herein will be described in detail, examples of which are illustrated by the accompanying structures and formulae. The disclosure intends to encompass all alternatives, modifications and equivalents, which are all within the scope of the appended claims provided herein. In addition, some of the technical features provided herein are clear and are described separately in multiple independent embodiments, but they can also be provided in a combination or any suitable sub-combinations form in an individual embodiment.

Compounds

The compound disclosed herein is a diaminoguanidine derivative of Formula (I), or a stereoisomer, geometric isomer, tautomer, solvate, pharmaceutically acceptable salt, or prodrug thereof, Formula (I)

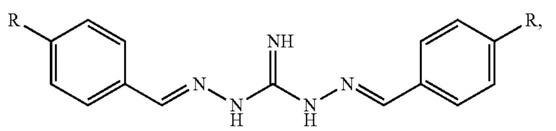

Formula (II)

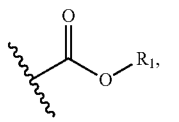

Formula (III)

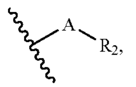

wherein R is a substituent at the 4-position on phenyl rings of Formula (I), and is $NO_2$, or has Formula (II) or Formula (III); $R_1$ is a linear or branched $C_1$-$C_{20}$ alkyl group; A is O, NH or S; and $R_2$ is a linear or branched $C_3$-$C_{14}$ alkyl group, $C_5$-$C_6$ cycloalkyl, substituted or unsubstituted $C_5$-$C_6$ aryl, or —$CH_2$($C_5$-$C_6$ aryl).

In principle, "substituted" refers to that one or more hydrogen atoms in the given structure are substituted with specific substituents. A substituted group can be substituted at each position of the group with a substituent, when the given structure can be substituted with one or more substituents at more than one positions, then the substituents can be same or different, substituted at each position.

The term "prodrug" as used herein refers to a compound that can be converted to the one according to Formula (I) in vivo. Such conversion is affected by the hydrolysis of the prodrug in the blood or the enzymatic conversion of the prodrug into the parent structure in the blood or tissues.

The term "$C_a$-$C_b$ alkyl group" as used herein refers to a linear or branched, saturated alkyl group containing a to b carbon atoms, such as methyl, ethyl, propyl, isopropyl, and the like. For example, "$C_1$-$C_5$ alkyl" means a linear or branched, saturated alkyl group containing 1 to 5 carbon atoms; and "$C_5$-$C_6$ cycloalkyl" means a cyclic alkyl group containing 5 or 6 carbon atoms and containing only both carbon and hydrogen, such as cyclopentyl, or cyclohexyl, or the like; "$C_5$-$C_6$ aryl" means a cyclic, aromatic group containing 5 or 6 carbon atoms, such as phenyl ring, and the like.

In some embodiments, R in the diaminoguanidine derivative is according to Formula (II), and $R_1$ is a linear $C_1$-$C_{20}$ alkyl group.

In further embodiments, $R_1$ is a linear $C_1$-$C_{12}$ alkyl group.

In an embodiment, R in the diaminoguanidine derivative is according to Formula (II), and $R_1$ is methyl.

In some embodiments, R in the diaminoguanidine derivative is according to Formula (II), and $R_1$ is a branched $C_1$-$C_{20}$ alkyl group.

In further embodiments, $R_1$ is a branched $C_3$-$C_4$ alkyl group.

In an embodiment, R in the diaminoguanidine derivative is according to Formula (II), and $R_1$ is isopropyl.

In some embodiments, R in the diaminoguanidine derivative is according to Formula (III).

Optionally, A is O, NH, or S.

In some embodiments, R in the diaminoguanidine derivative is according to Formula (III), and A is O.

In other embodiments, R in the diaminoguanidine derivative is according to Formula (III), and A is NH.

In some embodiments, R in the diaminoguanidine derivative is according to Formula (III), and $R_2$ is a linear or branched $C_3$-$C_{14}$ alkyl group.

Optionally, $R_2$ is a linear $C_3$-$C_{14}$ alkyl group.

In further embodiments, $R_2$ is a linear $C_3$-$C_{12}$ alkyl group.

In some embodiments, $R_2$ is n-propyl.

In other embodiments, $R_2$ is n-butyl.

And optionally, $R_2$ is a branched $C_3$-$C_{14}$ alkyl group.

In further embodiments, $R_2$ is a branched $C_3$-$C_5$ alkyl group.

In some embodiments, $R_2$ is isopropyl.

In some embodiments, R in the diaminoguanidine derivative is according to Formula (III), and $R_2$ is $C_5$-$C_6$ cycloalkyl.

In some embodiments, $R_2$ is cyclopentyl.

In some embodiments, R in the diaminoguanidine derivative is according to Formula (III), and $R_2$ is substituted or unsubstituted $C_5$-$C_6$ aryl.

In further embodiments, $R_2$ is unsubstituted $C_5$-$C_6$ aryl.

In an embodiment, $R_2$ is phenyl.

In further embodiments, $R_2$ is substituted $C_5$-$C_6$ aryl, which is optionally substituted with 1, 2, 3, 4 or 5 $R^3$, and $R^3$ is —OH, —$NH_2$, —$NO_2$, —CN, —SH, —X, —$C_1$-$C_5$ alkoxy, —$C_1$-$C_5$ alkyl, or $C_1$-$C_5$ alkyl substituted with X, wherein X is selected from F, Cl, Br, or I.

In particular embodiments, $C_5$-$C_6$ aryl is preferably phenyl.

In some embodiments, R in the diaminoguanidine derivative is according to Formula (III), and $R_2$ is substituted or unsubstituted —$CH_2$($C_5$-$C_6$ aryl).

In further embodiments, $R_2$ is unsubstituted —$CH_2$($C_5$-$C_6$ aryl).

In an embodiment, $R_2$ is benzyl.

In further embodiments, $R_2$ is substituted —$CH_2$($C_5$-$C_6$ aryl), and the aryl group is optionally substituted with 1, 2, 3, 4 or 5 $R^3$, and $R^3$ is —OH, —$NH_2$, —$NO_2$, —CN, —SH, —X, —$C_1$-$C_5$ alkoxy, —$C_1$-$C_5$ alkyl, or $C_1$-$C_5$alkyl substituted with X, wherein X is selected from F, Cl, Br, or I.

In particular embodiments, $R_2$ is substituted benzyl, and the phenyl ring on the benzyl group is optionally substituted with 1, 2, 3, 4 or 5 $R^3$, and $R^3$ is —OH, —$NH_2$, —$NO_2$, —CN, —SH, —X, —$C_1$-$C_5$ alkoxy, —$C_1$-$C_5$ alkyl, or $C_1$-$C_5$alkyl substituted with X, wherein X is selected from F, Cl, Br, or I.

In some of specific embodiments, the diaminoguanidine derivatives included herein comprise Compounds 1, 2, 3, and 4. The structures are shown as follows:

Formula (IV)

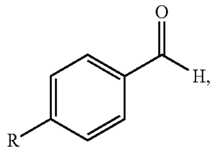

wherein R is a substituent at the 4-position on the phenyl rings of Formula (I), and is $NO_2$, or has Formula (II) or Formula (III); $R_1$ is a linear or branched $C_1$-$C_{20}$ alkyl group; A is O, NH, or S; and $R_2$ is a linear or branched $C_3$-$C_{14}$ alkyl group, $C_5$-$C_6$ cycloalkyl, substituted or unsubstituted $C_5$-$C_6$ aryl, or —$CH_2$($C_5$-$C_6$ aryl).

When R is a substituent with chirality, the benzaldehydes according to Formula (IV) will show certain chirality, and the products formed by reacting with diaminoguanidine may also possess chirality, will be present in different stereoisomeric or tautomeric forms.

When the diaminoguanidine derivatives produced by the reaction of the diaminoguanidine and the benzaldehydes

1

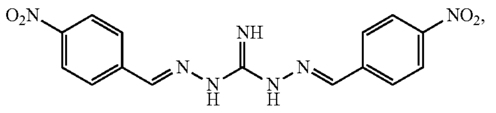

2

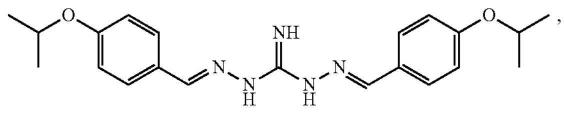

3

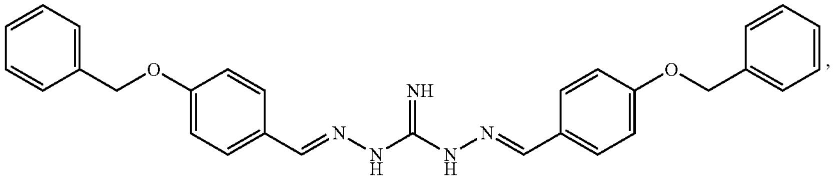

4

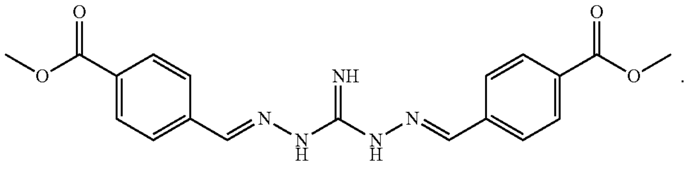

In some embodiments, the diaminoguanidine derivative is a pharmaceutically acceptable salt, and preferably a salt formed with an acid.

Optionally, the acid is an organic or inorganic acid.

Specifically, the inorganic acid includes, but is not limited to, sulfuric acid, methanesulfonic acid, hydrochloric acid, or phosphoric acid, and the organic acid includes, but is not limited to D,L-lactic acid, 2-hydroxyethylsulfonic acid, citric acid, tartaric acid, benzoic acid, succinic acid, fumaric acid, maleic acaid, acetic acid, or oxalic acid.

Preparation and Purification of Compounds

The diaminoguanidine derivative disclosed herein is a series of compounds obtained by the Schiff base reaction between diaminoguanidine and 4-substituted benzaldehyde, the methodology is described in CN103880712A, and the 4-substituted benzaldehyde is according to Formula (IV), according to Formula (IV) are in rigid configurations, the reaction substrate can yield different geometric isomers during the reaction process.

The aforementioned stereoisomers, geometric isomers, and tautomers are also encompassed within the scope of embodiments herein.

The term "stereoisomer" as used herein refers to a compound with the same chemical structure but different arrangements of atoms or groups in space, including enantiomers, diastereomers, conformational isomers, geometric isomers, atropisomers, and the like. The term "enantiomers" refer to two isomers of a compound that cannot be superimposed but are mirror images of each other. The term "diastereoisomers" refer to stereoisomers that have two or more chiral centers and whose molecules are not mirror images of each other, and have different physical properties such as melting points, boiling points, spectrum properties, and reactivity. The mixture of diastereoisomers can be isolated by high-resolution analysis operations such as electrophoresis or chromatography. The term “tautomers” refer to structural isomers with different energies that can be converted into each other through a low energy barrier.

In some embodiments, provided herein is a process for preparing the diaminoguanidine derivative, which involves the separation, purification or recrystallization process of the reaction product. The reaction product can be obtained as a crude product from the reaction by the solvent removal method. In order to obtain a solid substance with higher chemical purity and lower impurity content, the crude product is dissolved, crystallized or precipitated or recrystallized and separated in alcohol solvent, alcohol-water mixed solvent or other organic solvents that can be used for product recrystallization under suitable temperature, light environment and mechanical shaking conditions to obtain a diaminoguanidine derivative with a certain crystal form. The diaminoguanidine derivative with a certain crystal form is a diaminoguanidine derivative crystal or a solvate of the diaminoguanidine derivative. The solvate of the diaminoguanidine derivative can be selected from a hydrate or an ethanolate of the diaminoguanidine derivative.

The “solvate” as used herein refers to a co-crystal associate formed by complexing stoichiometric or non-stoichiometric solvent molecules through non-covalent intermolecular forces resulted from the external and internal conditions during contacting the compound herein with the solvent molecules. Solvents that form solvates include, but are not limited to, water, acetone, ethanol, methanol, dimethyl sulfoxide, ethyl acetate, acetic acid, isopropanol, and the like. “Hydrate” is an associate or crystal formed by complexing water, that is, a compound that complexes stoichiometric or non-stoichiometric water through non-covalent intermolecular forces.

The preparation of the diaminoguanidine derivative provided herein can also be worked up by a salting-out method in order to obtain a solid substance with higher chemical purity and lower impurity content. The salting-out method is a process of using the principles of acid-base neutralization, acid-base coordination or acid-base chelation to make an amino acid derivative and a corresponding organic or inorganic base, or organic or inorganic acid to form a salt precipitate, thereby obtaining a pharmaceutically acceptable salt. The salt of inorganic acid includes, but is not limited to, hydrochloride, hydrobromide, phosphate, sulfate, nitrate, or a combination thereof.

The feed-acceptable salt is one formed by the diaminoguanidine derivative herein and an organic base, an inorganic base, an organic acid, or an inorganic acid that is non-toxic to animals. The “feed-acceptable” refers to a substance or composition that must be chemically or toxicologically suitable, and is related to the composition of the feed or to the farmed animal for consumption.

In some embodiments, during the work-up step of the salting-out precipitation of the diaminoguanidine derivative herein, the organic acid forms an acid-base coordinating salt and/or an acid-base chelating salt. The organic acids include, but are not limited to, acetic acid, maleic acid, succinic acid, mandelic acid, fumaric acid, malonic acid, malic acid, 2-hydroxypropionic acid, pyruvic acid, oxalic acid, glycolic acid, salicylic acid, glucuronic acid, galactitol acid, citric acid, tartaric acid, aspartic acid, glutamic acid, benzoic acid, p-toluic acid, cinnamic acid, p-toluenesulfonic acid, benzenesulfonic acid, methanesulfonic acid, ethanesulfonic acid, or trifluoromethanesulfonic acid, or a combination thereof.

Pharmaceutical Compositions of the Invention

Provided herein is a feed composition comprising at least one of the diaminoguanidine derivative according to Formula (I), or a racemate, stereoisomer, geometric isomer, tautomer, solvate, or pharmaceutically acceptable salt thereof, and a pharmaceutically acceptable excipient, and the amount of the diaminoguanidine derivative in the composition can effectively control the conditions of a sick animal.

The term “composition” as used herein, refers to a set of compounds comprising one or more effective ingredients comprised of the compounds.

“Comprising” as used herein, refers to an open expression, which not only includes those specified herein, but does not exclude other aspects.

The pharmaceutically acceptable excipient is a pharmaceutically acceptable carrier, adjuvant, diluent, excipient, vehicle, dispersant, suspending agent, surfactant, isotonic agent, thickener, emulsifier, preservative, solid binder, or lubricant, or a combination thereof. “Carrier” as used herein, refers to a pharmaceutically acceptable substance that can carry active ingredients, improve its dispersibility, and have good chemical stability and adsorbability. The excipients provided herein include, but are not limited to, ion exchanger, aluminum stearate, lecithin, serum albumin, buffers such as phosphates, glycine, sorbic acid, potassium sorbate, a mixture of saturated plant fatty acid and glyceride, water, salts, electrolytes, protamine sulfate, disodium hydrogen phosphate, potassium hydrogen phosphate, sodium chloride, zinc salts, colloidal silicon, magnesium trisilicate, polyvinylpyrrolidone, polyacrylates, wax, lanolin, sugars, starch, celluloses and derivatives, gum powder, malt, gelatin, or talc; excipients are such as cocoa butter, or suppository wax; oils are such as peanut oil, cottonseed oil, safflower oil, sesame oil, olive oil, corn oil, or soybean oil; glycols are such as propylene glycol, or polyethylene glycol; esters are such as ethyl oleate, ethyl laurate, or agar; buffers are such as magnesium hydroxide, or aluminum hydroxide; lubricants such as alginic acid, ethanol, phosphate buffer solution, or sodium laurate; coloring agents coating materials; sweeteners; flavoring agents; perfuming agents; preservatives; and antioxidants.

The adjuvant is a wetting agent that induces the inherent viscosity of the substance, a binder that binds the substance together, a disintegrant that breaks the entire sheet of the substance into many fine particles, and a retention aid that reduces friction between particles or an anti-sticking agent that prevents material sticking, including but not limited to magnesium stearate, talc, vegetable oil, magnesium lauryl sulfate, starch, starch slurry, water, inorganic salt, dextrin, powdered sugar, and the like.

“Vehicle” as used herein, refers to the solvent required to dissolve or disperse solids, including but not limited to, water, ethanol, glycerin, and the like.

In some embodiments, the pharmaceutical composition further comprises one or more therapeutic agents.

The therapeutic agent includes, but is not limited to, a pharmaceutical feed additive, such as anthelmintic health care agents, veterinary antibiotics, or Chinese herbal medicines and the like.

Specifically, the pharmaceutical feed additive includes, but is not limited to, a veterinary acceptable premix material that can be incorporated into a carrier or diluent and has the effects of preventing animal diseases and promoting animal growth and can be added to feed for a long time.

More specifically, the pharmaceutical feed additive is a feed antibiotic, which includes but not limited to, polymyxin, salinomycin, avilamycin, bacitracin, virginiamycin, nosiheptide, flavomycin, enramycin, kitasamycin, olaquindox, oxytetracycline, or chlortetracycline.

Use of Diaminoguanidine Derivatives and Pharmaceutical Compositions Thereof

Provided herein is use of the above-mentioned diaminoguanidine derivative and a pharmaceutical composition comprising the same in the preparation of a medicament for an animal.

In some embodiments, the medicament is an agent useful for preventing a disease caused by bacterial infection.

In some embodiments, the medicament is an agent useful for preventing a disease caused by bacterial infection.

In some embodiments, the medicament is an agent useful for treating a disease caused by bacterial infection.

In some embodiments, the medicament is an agent useful for alleviating the symptoms of a disease caused by bacterial infection.

Optionally, the bacteria are Gram-positive bacteria, including but not limited to *Streptococcus pneumoniae, Staphylococcus aureus, Staphylococcus epidermidis, Streptococcus hemolyticus, Enterococcus*, and *Streptococcus viridans*.

Further, the bacteria are preferably *Staphylococcus aureus*.

In some embodiments, the disease caused by bacterial infection is a skin infection caused by *Staphylococcus aureus*.

In some embodiments, the disease caused by bacterial infection is a gastrointestinal infection.

In some embodiments, the disease caused by bacterial infection is a respiratory infection.

In some embodiments, the disease caused by bacterial infection is a genitourinary system disease, including mastitis, endometritis, urethritis, and the like.

In some embodiments, the diaminoguanidine derivative or a pharmaceutical composition thereof is in a specific dosage form in the preparation of a medicament for an animal.

Optionally, the specific dosage form includes, but is not limited to, oral dosage form, injection dosage form, suppository, topical dosage form, or perfusate.

Specifically, the specific dosage form comprises a therapeutically effective amount of a diaminoguanidine derivative in addition to a pharmaceutical excipient.

More specifically, the specific dosage form has a specific independently usable specification according to the regularity of clinical medication.

Methods of Animal Treatment

Provided herein is a method for treating a disease caused by bacterial infection in an animal.

Optionally, the method includes, but is not limited to, oral or injection administration of a pharmaceutical formulation of a diaminoguanidine derivative or a pharmaceutical composition thereof to an animal.

Further, the pharmaceutical formulation includes, but is not limited to, tablet, capsule, injection, liquid, pill, patch, and the like.

Still further, the formulation comprises different doses of a diaminoguanidine derivative according to the needs of effective doses at different animal growth stages.

The "effective dose" of the diaminoguanidine derivative or pharmaceutical composition herein is an effective amount for treating or alleviating the severity of one or more of the diseases described herein.

In some embodiments, the animal is pet, domestic animal or poultry at various growth stages.

Optionally, the pet includes but is not limited to, dog or cat; the domestic animal includes but is not limited to pig, cow, sheep, donkey or horse at various growth stages; the poultry includes but is not limited to chicken, duck, goose, or quail.

In some embodiments, the method of treatment comprising the diaminoguanidine derivative or the pharmaceutical composition thereof further comprises administering an additional therapeutic agent to the diseased animal, wherein the additional therapeutic agent includes, but is not limited to, chemotherapy, anti-inflammatory agent, traditional Chinese medicine, physical therapy, and the like. The additional therapeutic agent is suitable for the disease to be treated, wherein the additional therapeutic agent can be administered in combination with the diaminoguanidine derivative or the pharmaceutical composition described herein. The diaminoguanidine derivative or the pharmaceutical composition described herein is a single dosage form, or a separate compound or composition as a part of a multiple dosage form. The additional therapeutic agent may or may not be administered concurrently with the diaminoguanidine derivative described herein.

In order to make the objects, technical solutions, and advantages provided herein clearer, the following examples illustrate the compounds, compositions and uses herein in further detail. It should be understood that the specific examples described herein are only used to construe the present invention, but not limiting.

Example 1

Efficacy of Diaminoguanidine Derivatives on Endometritis in Postpartum Sows

Sows suffering from endometritis in 5 different pig farms were selected, 30 cases in each farm, 150 cases in total, were randomly divided into groups, and a non-treatment control was set up, and the sick pigs in each experimental group were perfused into the uterus. Agents, the main components of the uterine perfusion for treatment groups 1-4 were Compound 1, Compound 2, Compound 3, and Compound 4, respectively, at a dose of 10 mg/kg, and the control group was given an equal volume of normal saline. The frequency of administration is once a day for 7 consecutive days. The treatment effects are shown in Table 1.

TABLE 1

Efficacy of diaminoguanidine derivatives

| Groups | | Number of animals | Treatment effects | Cure rate |
|---|---|---|---|---|
| Control group | — | 30 | deterioration | — |
| Treatment group 1 | Compound 1 | 30 | 27 sows were cured, 1 sow improved in symptoms | 93.3% |
| Treatment group 2 | Compound 2 | 30 | 29 sows were cured, 1 sow improved in symptoms | 100% |
| Treatment group 3 | Compound 3 | 30 | 25 sows were cured, 2 sows improved in symptoms | 90.0% |
| Treatment group 4 | Compound 4 | 30 | 25 sows were cured, 5 sows improved in symptoms | 100% |

The experimental results show that 150 sick pigs suffering from endometritis in 5 pig farms were randomly selected in the experiment and divided into treatment group and untreated control group. After uterine infusion and agent administration, they were observed for 7 consecutive days.

The condition of sick pigs in the treatment group is effectively treated or improved, and the cure rate is as high as 90%. The condition of sick pigs in the untreated control group worsened.

Example 2

Efficacy of Compound 2 on Mastitis in Postpartum Sows

In the pig farming laboratory, postpartum sows have experienced redness, swelling and heat pain in the udders, refusal to let the piglets eat milk, increased body temperature, lack of energy, loss of appetite or extinction, reduced lactation, and thin watery colostrum, which later became the thick juice sample containing flocs and other phenomena for experimental treatment. They were then divided into two groups, each with 10 heads, corresponding to the control group and the experimental group, respectively. The control group received intramuscular injection of 500,000 units/head of penicillin and 500,000 units/head of streptomycin once a day for 5 consecutive days. The test group added compound 2 to the diet at 10 mg/kg·w each time, twice a day for 5 consecutive days. The results are shown in Table 2.

TABLE 2

Treatment effects of Compound 2 on mastitis in postpartum sows

| Groups | Symptoms before treatment | Symptoms after treatment | Cure rate |
|---|---|---|---|
| Control group | Breast swelling and pain, do not allow piglets to eat milk, increase in body temperature, lack of energy, loss of appetite or abolishment, reduced lactation, diseased colostrum looks thin and watery, and then becomes thick and thick with flocci. | Some sick pigs' breasts are red, swollen and painful, so piglets are not allowed to eat milk, body temperature rises, lack of energy, loss of appetite or annihilation, reduced lactation, sick colostrum looks thin and watery, and then becomes thick juice with flocci and other symptoms basically disappeared or completely disappeared. | 64.57% |
| Test group | Breast swelling and pain, do not allow piglets to eat milk, increase in body temperature, lack of energy, loss of appetite or abolishment, reduced lactation, diseased colostrum looks thin and watery, and then becomes thick and thick with flocci. | Some sick pigs' breasts are red, swollen and painful, so piglets are not allowed to eat milk, body temperature rises, lack of energy, loss of appetite or annihilation, reduced lactation, sick colostrum looks thin and watery, and then becomes thick juice with flocci and other symptoms basically disappeared or completely disappeared. | 93.07% |

The results show that Compound 2 has good treatment effects on mastitis in a postpartum sow, with a cure rate of more than 90%, and the treatment effects are better than that of intramuscular injection of penicillin and streptomycin.

Example 3

Efficacy of Compound 2 on Skin Infection in Mice

Each mouse was placed in an induction box for isoflurane induction anesthesia, a piece of back fur was cut to expose the skin, and a round piece of skin was removed with a hand-held punching machine, leaving a wound with a central cavity on the back. The wound was inoculated and infected with 10 μL of $2.5*10^{-7}$ CFU/mL *Staphylococcus aureus* suspension. The mice were placed in each recovery box marked with a mouse number, and the time of inoculation and the initial body weight of the mice were recorded. When the mice returned to a fully conscious state, they were returned to each cage for 4 hours of postoperative or anesthetic complications monitoring. Approximately 4-6 hours after infection, the wound was locally treated with 0.2 g of vehicle or 20 mg/g of Compound 2, and the infected skin wound was treated again every 12 hours, a total of 14 treatments, continuous monitoring observe for 7 days. 7 days later, the mice were euthanized, the original infected wound area was dissected and removed, and the bacterial content was tested by standard microbiology, and the harvested strain was confirmed to be *Staphylococcus aureus*. The result of the test was that the average colony count per gram of tissue observed in the vehicle treatment group was 5381475, and the average colony count per gram of tissue observed in the Compound 2 treatment group was 2207, and the reduction percentage of colony count per gram of tissue is shown in Table 3.

TABLE 3

Treatment effects of Compound 2 on bacterial wounds in mice

| Groups | CFU/g | Reduction (%) |
|---|---|---|
| Vehicle treatment group | 5381475 | — |
| Compound 2 treatment group | 2207 | 99.96 |

It can be seen from the results that the treatment with Compound 2 resulted in a significant decrease in the number of infectious *Staphylococcus aureus*, which proved that compound 2 was effective in treating skin infection in a mouse.

Example 4

Safety Evaluation of Compound 2

Example 4.1 Acute Oral Toxicity Assay of Compound 2 in Rats

1 Materials and Methods 1.1 Experimental Material

Experimental animals: 40 clean-grade healthy Wistar rats, weighing 160-200 g, half female and half male, provided by the Comparative Medicine Center of Yangzhou University.

Test article: Compound 2, provided by Guangzhou Insighter Biotechnology Co., Ltd., was made into a suspension of the required concentration with 1% sodium carboxymethyl cellulose solution immediately before use.

Method of administration: The method of administration is oral administration, the volume of the test article given is 1.0 mL/100 g of b.w., no feeding is allowed for 12 hours before administration, no drinking water is restricted, and feeding is 3 hours after administration.

1.2 Experimental Procedure 1.2.1 Pre-Experiment

Each group has 4 rats (female and half male) for pre-test, 4/4 lethal dose (b) and 0/4 lethal dose (a) are measured. The lethal dose of Compound 2 to rats was determined to be a=700 mg/kg b.w. and b=5000 mg/kg b.w. in the pre-test for 0/4 lethal dose and 4/4 lethal dose, respectively.

1.2.2 Normal Experiment

Generally, there are 5 to 7 dose groups. The number of formal test groups (N) is determined according to the ratio of the 4/4 lethal dose (b) and the 0/4 lethal dose (a) obtained in the pre-test. When the ratio is 2 to 3, 4 to 5 groups were set; the ratio is 3~10, 5~7 groups were set. This experiment has 6 dose groups.

The dose ratio (r) of the adjacent two groups is calculated according to the below equation:

$$r = \sqrt[n-1]{\frac{b}{a}}$$

wherein r is the ratio of the adjacent two groups of doses, b is the minimum total lethal dose, a is the highest non-lethal dose, n is the number of groups. According to this equation, the r value in the rat oral acute toxicity test was calculated to be 1.48.

The 4/4 lethal dose (b) obtained in the pre-test was used as the dose of the normal test high-dose group (the first group), and the doses of the other dose groups were calculated according to the ratio of r value.

Experimental animal group: 60 clean-grade healthy Wistar rats were randomly divided into 6 groups using a complete randomization method, each group with 10 rats, half male and half male, and the male and female animals were separated for formal test.

Preparation of test article solution: The test article solution required by each dose group of rats according to the equal volume of "LK serial dilution method" was prepared according to the designed test dose. According to the requirements of the volume of the test article given to the test animal, both the concentration C1 of the test article solution required for the maximum dose group and the volume m of the test article solution required for each dose group were firstly determined.

The concentration (C) that the mother liquor of the test article is C1, and the volume (M) that should be prepared according to:

$$M = \frac{m}{1-K},$$

where K is the ratio of the doses of each group, K=1/r.

The amount of test article (mg or mL) should be weighed according to the concentration and volume of the mother liquor.

The test article was weighted and placed into a beaker, the selected solvent (1% sodium carboxymethyl cellulose solution) was added to dissolve or dilute before being transferred into a volumetric flask with full mixing and determining the constant volume to obtain the mother liquor of the test article with a concentration of C=C1. The solution volume m for administration of the highest dose group was taken out, and the same volume of solvent was added to the original solution. After mixing, the concentration of the solution is C1×K, which is exactly the dose concentration C2 required by the next-high dose group; The volume of the solution used for the second group is m, and then the same volume of solvent is added. After mixing, the concentration of the solution is C2×K, which is exactly the dose concentration C3 required by the third group. Concentration and volume for each dose of the test article solution were then calculated like this.

The oral administration doses of Compound 2 in groups 1 to 6 were 700 mg/kg, 1037 mg/kg, 1537 mg/kg, 2277 mg/kg, 3374 mg/kg, and 5000 mg/kg, respectively.

Experimental observation: After the administration, the general conditions of the rats were observed twice a day, including body weight, mental state, coat color, autonomous activities, breathing, desire to eat, feces, oral and nasal secretions, symptoms of poisoning and death. During the observation period, the dead rats were subjected to gross anatomical examination, and all gross pathological changes were recorded. The observation was continued for 14 days. After the test, the surviving rats were sacrificed and the symptoms of necropsy were observed.

1.2.3 Data Collection

According to the test records, various data were sorted out and obtained. The $LD_{50}$ value and the 95% confidence limit were calculated following the below equation by the modified Kber method.

$$LD_{50}=\log^{-1}[X_m-i(\Sigma p-0.5)]$$

When mortality is not 0% or 100% mortality, $LD_{50}$ should be calculated according to equations below:

$$LD_{50} = \log^{-1}\left[X_m - i\left(\sum p - \frac{3-P_m-P_n}{4}\right)\right];\quad S_{x50} = i\sqrt{\frac{\sum pq}{n}}$$

95% confidence limit of $LD_{50}$=log−1(log $LD_{50}$±1.96×S×50)

For above equations, i is the group distance, that is the difference between the logarithmic doses of the adjacent two groups of doses; Xm is the logarithm of maximum dose; P is the mortality in each dose group (determinants are expressed in decimals); Pm is the highest death rate; q is the dose survival rate of each group, q=1−p; Pn is the lowest death rate; Σp is the sum of mortality of each dose group; n is the number of animals in each group; Sx50 is the standard error of log $LD_{50}$.

1.2.4 Results and Evaluation

The toxicity classification of the test article was assessed according to the half-lethal dose ($LD_{50}$) of the test article and the acute toxicity ($LD_{50}$) dose grading table (Table 4).

TABLE 4

Dose classification of chemical acute toxicity ($LD_{50}$)

| Classification | Oral dose, $LD_{50}$ (rat, mg/kg) | Equivalent to human lethal dose (g/person) |
|---|---|---|
| Extremely toxic | <1 | 0.05 |
| Highly toxic | 1-50 | 0.5 |
| Moderately toxic | 51-500 | 5 |
| Low toxic | 501-5000 | 50 |

TABLE 4-continued

| Dose classification of chemical acute toxicity ($LD_{50}$) | | |
|---|---|---|
| Classification | Oral dose, $LD_{50}$ (rat, mg/kg) | Equivalent to human lethal dose (g/person) |
| Practically non-toxic | 5001-15000 | 500 |
| Non-toxic | >15000 | 2500 |

2. Experimental Results 2.1 Symptoms of Poisoning

The rats in the high-dose group appeared depressed, their fur were rough and dull, and gradually turned into inhibition, slow response, inability to eat, and paralysis after the oral administration for 25 min. After 0.5-1.0 h, the rats developed dyspnea, neck straightening, and loss of appetite. 3 h later, they began to die. The rats developed convulsions, convulsions, tremors and other neurological symptoms before death. Acute death occurred after administration for 3-24 hours. Dissection after poisoning death mainly manifests damage to the liver, followed by lungs and heart. The main changes of the liver include bleeding spots, congestion, edema, yellow-brown on the surface, and the like. The main pathological changes of the lungs are surface congestion and edema, and the like. The main pathological changes of the heart are the color of the myocardium and coronary artery congestion.

2.2 Acute oral $LD_{50}$ 14 days after the end of the administration, according to the mortality of each dose group (see Table 5), the acute oral $LD_{50}$ of compound 2 to rats was calculated to be 1870.83 mg/kg b.w., and the 95% credible limit of its $LD_{50}$ was 1516.98-2307.21 mg/kg b.w.

TABLE 5

| Statistics of rat mortality in acute toxicity test of Compound 2 by oral | | | | |
|---|---|---|---|---|
| Groups | Dose (mg/kg b.w.) | Number of animals | Number of dead animals | Mortality rate (%) |
| 1 | 700 | 10 | 0 | 0 |
| 2 | 1037 | 10 | 2 | 20 |
| 3 | 1537 | 10 | 3 | 30 |
| 4 | 2277 | 10 | 7 | 70 |
| 5 | 3374 | 10 | 8 | 80 |
| 6 | 5000 | 10 | 10 | 100 |

3. Conclusions

The acute oral $LD_{50}$ of Compound 2 obtained in this test for Wistar rats is 1870.83 mg/kg b.w. The oral acute toxicity of Compound 2 is low toxicity according to the acute toxicity ($LD_{50}$) dose classification table (Table 4).

Example 4.2 *Salmonella Typhimurium* Reverse Mutation Assay for Compound 2

Reagents: Compound 2 (isopropoxyphenylguanidine, batch number: 20150419), provided by Guangzhou Insighter Biotechnology Co., Ltd., sealed and stored at 4° C. for later use; standard mutagens are sodium azide, 2-aminofluorene, and dixone, All of them are analytical grade; sodium hydrogen phosphate, citric acid, dipotassium hydrogen phosphate, magnesium sulfate heptahydrate, sodium chloride, potassium chloride, magnesium chloride, sodium hydroxide, hydrochloric acid, disodium hydrogen phosphate, dimethyl sulfoxide, D-biotin, L-histidine, glucose, 6-phosphate glucose, reduced coenzyme II, agar powder, beef extract, tryptone, and the like, all of them are analytical reagents.

Instrument and Equipment: Double single-sided ultra-clean workbench, JA2003 electronic balance, SZ-2 automatic double distiller, QYC-200C air constant temperature shaker, D98-9052B-2 water-insulating electric heating constant temperature incubator, YXQ.SG41.280 portable type pressure steam sterilizer, micropipette (10 μL, 100 μL, 200 μL, 1000 μL), ultra-low temperature refrigerator (−80° C.), Centrifuge 5415R high-speed refrigerated centrifuge, electric heating constant-temperature water bath, D98-9052B-2 Electric heating constant-temperature incubator, colony counter, petri dish, and the like.

1.1. Medium and Reagent Preparation

Nutrient broth medium: 2.5 g of beef extract, 5.0 g of tryptone, 2.5 g of sodium chloride, and 1.3 g of dipotassium hydrogen phosphate ($K_2HPO_4.3H_2O$) were mixed and diluted to 500.0 mL with distilled water. After heating to dissolve, the pH was adjusted to 7.4 with 1N of sodium hydroxide solution. Then the mixture was autoclaved at 0.103 MPa for 20 min, and stored at 4° C. for later use.

Nutrient broth agar medium: 1.5 g of agar powder, 100.0 mL of nutrient broth medium. After heating and melting, the pH was adjusted to 7.4 with 1N of sodium hydroxide solution. Then the mixture was autoclaved at 0.103 MPa for 20 minutes, and poured into a petri dish (diameter 90 mm) while it is hot, about 25 mL/dish. After cooling and solidification, the mixture was incubated at 37° C. overnight to remove surface moisture and stored at 4° C. for later use.

Top medium: 78.0 mg of L-histidine (MW: 155) and 122.0 mg of D-biotin (MW: 244) were diluted to 1000.0 mL with distilled water. Each component was heated to dissolve biotin to obtain 0.5 mmol/L of histamine acid-biotin solution, which was then autoclaved at 0.068 MPa for 20 min, and stored at 4° C. for later use. 1.2 g of agar powder and 1.0 g of sodium chloride was dissolved and diluted to 200.0 mL with distilled water. The mixture was dispensed into sterile cuvettes after mixing, autoclaved at 0.103 MPa for 30 min, and stored at 4° C. for later use. The mixture was heated and melted before use, and 20 mL of 0.5 mmol/L histidine-biotin solution was aseptically added, mixed well, and dispensed into sterile small test tubes (2 mL per tube), and finally kept at 45° C. for later use.

1.1.5 Preparation of 10% S9 Mixture 1.65 mol/L of potassium chloride solution, 0.4 mol/L of magnesium chloride solution, 0.2 mol/L of phosphate buffer (pH 7.4), 0.025 mol/L of coenzyme II (oxidized type) solution and 0.05 mol/L glucose-6-phosphoric acid solution, potassium chloride, magnesium chloride and phosphate buffer solution are autoclaved at 0.103 MPa for 20 min, and stored in a refrigerator at 4° C. for later use. Coenzyme II (oxidized) solution and glucose-6-phosphate solution are filtered and sterilized, and then kept below −20° C. in a refrigerator for later use.

Each 10 mL of 10% S9 mixture containing the following components: 0.2 mol/L of phosphate buffer (pH 7.4) (6.0 mL), 1.65 mol/L potassium chloride solution (0.2 mL), 0.4 mol/L magnesium chloride solution (0.2 mL), 0.05 mol/L of glucose-6-phosphate solution (1.0 mL), 1.6 mL of 0.025 mol/L coenzyme II solution, and 1.0 mL of rat liver S9. The reagents were pre-cooled in an ice bath, then taken out according to their volume and added to a pre-cooled sterile test tube, mixed well, and put in an ice bath for later use.

1.2 Identification of Test Strains and their Biological Characteristics

Test strains: A set of standard test strains of TA97, TA98, TA100 and TA102 were provided by the Jiangsu Provincial Center for Disease Control and Prevention, and stored at −80° C. The test bacteria were cultured in a 37° C. water bath with shaking for 24 hours and stored at 4° C.

Enrichment culture: The main plate or the frozen-preserved strain culture was inoculated into nutrient broth, and cultivated for 10 hours at 37° C. with shaking (100 times/min). The strain culture should be more than $1\sim2\times10^9$ viable bacteria per milliliter.

Identification of biological characteristics: *Salmonella typhimurium*/reverse mutation assay (GB 15193.4-2003) standard method was used to detect the biological characteristics of test strains and the number of spontaneously reverting colonies. The results showed that the TA97, TA98, TA100 and TA102 standard test strains all meet the biological characteristics requirements of Table 6.

TABLE 6

Criteria for identification of test strains

| Strains | Histidine deficiency | Lipopolysaccharide barrier deficiency | R factor (Ampicillin resistance) | uvrB repair deficiency | Antitetracycline | Number of spontaneously reverting colonies (-S9) |
|---|---|---|---|---|---|---|
| TA97 | + | + | + | + | − | 90-180 |
| TA98 | + | + | + | + | − | 30-50 |
| TA100 | + | + | + | + | − | 120-200 |
| TA102 | + | + | + | − | + | 240-320 |
| Note: | "+": needing histidine | "+": inhibition zone | "+": having R factor | "+": no repair ability | "+": having tetracycline resistance | |

1.3 Induction of Rat Liver Microsomal Enzymes and Preparation of S9

2 healthy male adult SD rats were chosen with weight of 200-220 g, PCBs (Aroclor1254) was used as the inducer, and PCBs was dissolved in corn oil at a concentration of 200 mg/mL. 500 mg/kg b.w. solution was intraperitoneally injected into rats under sterile operation. The animals were given normal diet and drinking water every day after the induction, and the animals were sacrificed by cervical dislocation on the Day 5 after the induction, and the animals were stopped eating and drinking 12 hours before the sacrifice.

S9 was prepared by GB 15193.4-2003 method. 75% alcohol (4000 mL) was dispensed into two large containers with cover. Animals died in cervical spine was put in 1 #container with 75% alcohol (0-4° C.) to disinfect animal fur for 5 min. Then the animals were removed into 2 #continued by 75% alcohol (0-4° C.) to disinfect animal fur for another 5 min. In the ultra-net table of sterile chamber, the liver was cut out, and the liver connective tissue was removed. The liver was washed 5 times with the sterile 0.15 mol/L of potassium chloride solution (0° C.) with the addition of a sterile 0.15 mol/L of potassium chloride solution (0° C.) 3 ml according to the liver per gram. Hepatomy was made of tissue homogenizer (200000 r/min, 1 min). At 4° C., at 9000 g of hepatomy was centrifuged for 10 min, then the supernatant was taken into a sterile plastic tube (1 ml per tube). After sterile inspection, the protein content determination, the biological activity identification is further qualified at −80° C. for preservation.

1.4 Treatment of Sample and Test Method $LD_{50}$ was 1000 mg/kg of Compound 2 in rats. According to the physicochemical properties of the test article, the Compound 2 was prepared before test: 0.1 g of Compound 2 white powder was under UV sterilization for 2 h before test, and dissolved in 10 mL of dimethyl sulfoxide (DMSO), and then diluted to the desired concentration for the use (fresh preparation). The mutation assay (Ames test) method was used to detect the mutation of the sample by GB15193.4-2003.

1.5 Positive Control by Point Test Method

On the base of each piece of paper having the saturation water absorption of 0.01 mL, with the addition of S9, TA97, TA98, TA100, and TA102 strains are added with 2-acetyl aminool (2-AF) with the concentration of 2 mg/mL. Without the addition of S9, TA97 and TA98 strains are added with Dixon with the concentration of 5 mg/mL, the TA100 strain was used for 1 mg/mL diluted with 4-nitroquinoline-N-oxide, and the TA102 strain was used for 0.2 mL/ml diluted with methyl methanesulfonate. For the plate incorporation test, when S9 was added, the TA97, TA98, TA100, and TA102 strains were at a concentration of 100 μg/mL (10 μg/100 μL dish) after diluted with 2-acetamidofluorene (2-AF). When S9 was not added, the TA97 and TA98 strains were at a concentration of 0.5 mg/mL after diluted with Dixon. TA100 strain was at a concentration of 5 μg/mL diluted with 4-nitroquinoline-N-oxide. TA102 strain was at a concentration of 10 μL/mL diluted with methyl methanesulfonate.

1.6 Plate Incorporation Test

Dose group design: 1 mg/100 μL·dish is for determining the highest dose of the plate-incorporation method test. There are 4 dose groups, and a negative (solvent) control group and a positive control. Each dose is divided into two series with S9 (+S9) and without S9 (−S9), and 3 parallel plates are designed.

Preparation of test agent solution: 0.1 mL of test agent solution was added to each dish, and the highest concentration and volume of test agent solution to be prepared were determined according to the set maximum test dose of 10 mg/mL. The amount of the test agent to be weighed was calculated when the solution was prepared. Accurate 0.1 g of the test agent was weighted into the reagent bottle, an appropriate amount of DMSO was introduced to dissolve it, then transferred into a 10 mL volumetric flask, mixed and diluted to 10 mL. Thus the test agent solution required by the highest dose group of the test is obtained. A sufficient amount for the test of the highest dose group was divided, and the remaining solution was diluted with DMSO successively, therefore the test agent solutions required for the remaining 4 dose groups are available.

Test operation: 192 bottom medium plates were selected as spares, divided into 4 strains to repeat, repeating 8 groups each one, 6 plates in each group, and the plates were marked well. A tube (2 mL) of the top culture medium that has been melted and kept in a water bath at 45° C. was taken, a pipette was used to add 0.1 mL of the test agent solution and 0.1 mL of the test bacteria solution (+S9 group at the same time was added 0.5 mL of 10% S9 mixture), the mixture was followed by quick mixing, poured on the bottom culture medium, the petri dish was rotated to evenly distribute the top culture medium on the bottom layer, then was laid flatly, solidified, and incubate at 37° C. for 48 hours to observe the results. If the result of the first plate incorporation method is negative, the test needs to be repeated again; if the result of the first plate incorporation method is positive, the test needs to be repeated two more times.

concentration of the test agent in the test group reaches 1 mg/100 μL dish, there is no statistical difference in the number of mutant colonies per dish compared with the negative control, which can be considered as negative for mutagenesis. At least three repeated tests should be performed for positive results, and at least two repeated tests for negative results in order to make the final evaluation of the test drug. The results of the spot test method of the test agent shall be confirmed by the plate incorporation method. If the test agent for the plate of 4 strains (with S9 and without S9) shows negative results, it can be considered that the test agent is not mutagenic to *Salmonella typhimurium*. If the test agent is mixed with one or more strains (with or without S9) in the plate and the result is positive, the test agent is considered to be a mutagen of *Salmonella typhimurium*.

TABLE 7

Results of the *Salmonella typhimurium* reverse mutation assay for Compound 2 $\bar{x} \pm SD$ (First)

| | $TA_{97}$ | | $TA_{98}$ | | $TA_{100}$ | | $TA_{102}$ | |
|---|---|---|---|---|---|---|---|---|
| Groups | $-S_9$ | $+S_9$ | $-S_9$ | $+S_9$ | $-S_9$ | $+S_9$ | $-S_9$ | $+S_9$ |
| 1 mg/dish | 154.33 ± 11.93 | 149.67 ± 36.67 | 38.00 ± 2.65 | 39.33 ± 6.51 | 170.00 ± 2.00 | 162.33 ± 9.87 | 277.33 ± 16.77 | 268.67 ± 14.47 |
| 0.2 mg/dish | 158.67 ± 2.31 | 134.00 ± 9.17 | 42.33 ± 9.87 | 36.33 ± 5.03 | 168.33 ± 8.02 | 158.33 ± 6.51 | 284.67 ± 4.16 | 270.67 ± 4.51 |
| 0.04 mg/dish | 144.00 ± 4.36 | 154.00 ± 19.08 | 41.00 ± 7.00 | 32.67 ± 1.53 | 168.33 ± 4.16 | 164.67 ± 8.33 | 276.33 ± 8.02 | 268.67 ± 11.93 |
| 0.008 mg/dish | 147.33 ± 23.01 | 159.67 ± 7.37 | 40.00 ± 3.00 | 45.33 ± 2.08 | 154.33 ± 13.58 | 148.33 ± 4.04 | 269.67 ± 10.97 | 257.67 ± 5.51 |
| 0.0016 mg/dish | 156.33 ± 10.69 | 155.67 ± 6.35 | 37.00 ± 2.00 | 41.67 ± 5.03 | 162.33 ± 4.93 | 140.00 ± 4.36 | 271.00 ± 9.64 | 263.67 ± 5.69 |
| DMSO | 141.00 ± 8.67 | 128.67 ± 35.10 | 41.00 ± 6.00 | 40.00 ± 5.57 | 163.00 ± 17.6 | 146.00 ± 7.00 | 267.33 ± 21.36 | 274.67 ± 16.26 |
| Positive control | Dixon (50 μg) | 2-AF (10 μg) | Dixon (50 μg) | 2-AF (10 μg) | $NaN_3$ (1.5 μg) | 2-AF (10 μg) | Methyl Methanesulfonate (1.0 μL) | 2-AF (10 μg) |
| | >2000 | 1398.00 ± 87.68 | 932.00 ± 57.17 | >2000 | >2000 | >2000 | 392.67 ± 12.86 | 392.67 ± 12.86 |

Note:
The dose of the control in parentheses following the positive control is (μg/100 μL dish or μL/100 μL dish), similarly hereinafter.

TABLE 8

Results of the *Salmonella typhimurium* reverse mutation assay for Compound 2 $\bar{x} \pm SD$ (Second)

| | $TA_{97}$ | | $TA_{98}$ | | $TA_{100}$ | | $TA_{102}$ | |
|---|---|---|---|---|---|---|---|---|
| Groups | $-S_9$ | $+S_9$ | $-S_9$ | $+S_9$ | $-S_9$ | $+S_9$ | $-S_9$ | $+S_9$ |
| 1 mg/dish | 157.00 ± 4.36 | 152.00 ± 23.58 | 38.67 ± 3.51 | 33.33 ± 2.52 | 163.33 ± 23.69 | 160.33 ± 10.41 | 281.33 ± 23.03 | 267.33 ± 23.86 |
| 0.2 mg/dish | 151.00 ± 14.11 | 128.33 ± 7.37 | 39.67 ± 5.51 | 37.67 ± 6.03 | 171.00 ± 7.55 | 166.00 ± 3.00 | 279.33 ± 1.53 | 264.33 ± 8.96 |
| 0.04 mg/dish | 155.67 ± 6.66 | 152.33 ± 17.79 | 35.67 ± 4.16 | 38.67 ± 2.52 | 169.00 ± 1.00 | 165.33 ± 10.07 | 270.67 ± 6.66 | 277.67 ± 9.02 |
| 0.008 mg/dish | 166.33 ± 3.06 | 154.67 ± 8.33 | 42.67 ± 3.21 | 36.00 ± 3.61 | 159.33 ± 9.29 | 141.33 ± 3.51 | 271.00 ± 13.23 | 264.00 ± 14.11 |
| 0.0016 mg/dish | 164.00 ± 6.25 | 145.67 ± 8.96 | 41.33 ± 3.21 | 44.67 ± 6.66 | 164.67 ± 8.33 | 145.33 ± 7.23 | 272.00 ± 13.00 | 267.67 ± 12.42 |
| DMSO | 134.00 ± 38.30 | 131.00 ± 30.45 | 43.33 ± 2.52 | 41.00 ± 4.00 | 156.33 ± 14.98 | 138.67 ± 11.68 | 263.00 ± 22.11 | 263.33 ± 6.66 |
| Positive control | Dixon (50 μg) | 2-AF (10 μg) | Dixon (50 μg) | 2-AF (10 μg) | $NaN_3$ (1.5 μg) | 2-AF (10 μg) | Methyl Methane-sulfonate (1.0 μL) | 2-AF (10 μg) |
| | >2000 | 939.33 ± 15.53 | >2000 | >2000 | >2000 | >2000 | >2000 | 393.33 ± 5.86 |

Judgment and evaluation of results: The results of each test were sorted out, and the number of strains turned into colonies was expressed as ($\bar{x}$±SD)/dish. If the number of spontaneous reverting colonies per dish in the negative control is within the normal range, the number of reverting colonies per dish in the test group will increase by more than 1 time (that is, the number of reverting colonies in the test group is equal to or greater than twice the number of reverting colonies in the negative control), and if there is a dose-reverse relationship or at least a repetitive and statistically significant positive reaction at a certain test point, the test agent can be considered as mutagenic positive; when the

2 Results

The results of the two repeated tests are shown in Table 7 and Table 8. The four kinds of *Salmonella typhimurium* strains used in the test grew normally, and the average number of reverted colonies of each strain in the positive control test exceeded twice the average number of reverted colonies of the corresponding negative control, confirming that the histidine auxotrophic mutant strain of *Salmonella typhimurium* was effective in the detection of the test article, and the reaction of each strain was qualified. When the dose of Compound 2 per dish was within the range of 1 mg-0.0016 mg, with or without metabolic activation system (S9), the average number of colonies per dish of the four *Salmonella typhimurium* test strains was within twice that of the solvent control, showing no dose-reverse relationship and the results of the two experiments are consistent, indicating that compound 2 has no mutagenic activity with or without S9, and is not mutagenic to *Salmonella typhimurium.*

Example 4.3 Micronucleus Assay of Compound 2 in Bone Marrow Cells of Mice

1 Materials and Methods 1.1 Materials

Experimental animals: 60 clean and healthy ICR mice have the average weight of 18-20 g, half female and half male, purchased from the Comparative Medicine Center of Yangzhou University.

Regents: The test drug Compound 2, provided by Guangzhou Insighter Biotechnology Co., Ltd., was prepared into a suspension of 1.0% sodium carboxymethyl cellulose at the required concentration before use; the mutagenic positive control chemical is cyclophosphamide with the content of 99.00%; Methanol, glycerol, potassium dihydrogen phosphate, and Giemsa dyes are all analytically pure; calf serum, filtered and sterilized, placed in a constant temperature water bath at 56° C. for 1 hour for inactivation, and stored at 4° C. for later use; Giemsa storage solution is self-preparation; 1/15 mol/L phosphate buffer (pH 6.8) is self-preparation; Giemsa working solution is prepared by mixing 1 part of Giemsa stock solution and 6 parts of 1/15 mol/L phosphate buffer (pH 6.8), freshly prepared just before use.

Equipment: Benchtop centrifuge, biological microscope (with 100× oil lens), constant humidity water bath (temperature control error ±0.5° C.), cell counter, dissecting equipment, glass slides, syringes, gastric gavage needles and other common laboratory equipment.

1.2 Procedures

Dosage group design: 60 mice were randomly divided into 5 groups according to the set number of groups, with 12 mice in each group (half males and half females, and males and females in separate cages) for experiment. The administration of toxicant by oral $LD_{50}$ of Compound 2 to mice is 1000 mg/kg. According to the $LD_{50}$ of Compound 2 and its physical and chemical properties, the test is set to 500 mg/kg body weight (high), 250 mg/kg body weight (medium), and 125 mg/kg body weight (low) dose groups. There is also a positive control and a negative (solvent) control. Cyclophosphamide was selected for the positive control at a dose of 40 mg/kg b.w.

Preparation of test article solution: The test agent, Compound 2 was diluted with 1.0% sodium carboxymethyl cellulose as a solvent, and it was given by oral in different concentrations and the same volume with the fresh preparation and use.

Administration: Intragastric administration method is used for two administrations with an interval of 24 hours between the two administrations. For each administration, the body weight of the mice was weighed, the test article was given to the mice according to the requirements of 0.1 mL/10 g b.w., the test article suspension was drawn with a syringe and administered each mouse by gavage. The cyclophosphamide 40 mg/kg b.w. (0.1 mL/10 g b.w.) was selected for positive control through intraperitoneal injection. The 0.5% sodium carboxymethyl cellulose solution was selected for negative control, and the oral volume was 0.1 mL/10 g b.w.

Specimen preparation: 6 hours after the second administration of the test article, 5 female rats and 5 male rats in each group were sacrificed by cervical dislocation. The femurs on both sides of each mouse and muscles were removed, the blood stains on the surface were wiped off with filter paper or gauze, and both ends of the femur were cut off. A 1 mL syringe equipped with a 6-gauge needle to was used to draw about 0.2~0.5 mL of calf serum to flush the bone marrow cavity several times, and then the flushing substance was dropped on the correspondingly numbered slide. After the bone marrow cavity rinses on the slides was mixed thoroughly, the slides were pushed, 2 sheets per mouse, and dried quickly. The dried smear was fixed in methanol for 5-10 min, and then taken out to dry. The fixed smear is stained with Giemsa application solution for 15-30 min, rinsed with distilled water, dried, and gets ready for inspection.

1.3 Data Collection and Analysis

The film was read by double-blind method, the number of polychromatic red blood cells (PCE) of each mouse was recorded in each group, including the number of micronucleus PCE cells, and the number of mature red blood cells (RBC), and the like. The number of polychromatic red blood cells (PCE) was calculated, including the number of micronucleus PCE cells and the number of mature red blood cells (RBC) in each test group of male and female mice respectively, and the results were listed.

The PCE micronucleus rate and PCE/RBC ratio of each test group of male and female mice were calculated according to the following Formula, and their respective standard deviations were calculated and the results were tabulated.

$$\text{Micronucleus rate of polychromatic erythrocytes } (\%\,o) = \frac{\text{Total number of polychromatic erythrocytes with micronuclei}}{\text{Check the total number of polychromatic red blood cells}} \times 1000\%$$

The experimental data is processed by SPSS 11.0 statistical software, and the analysis result is expressed as $\overline{x}$±SD, and the incidence of micronucleus is statistically processed according to the $X^2$ test (α=0.05).

2 Results

The experimental results are shown in Table 9 and Table 10. The ratio of polychromatic red blood cells to mature red blood cells (PCE/RBC) in each group was within the normal range. Compared with the negative (solvent) control, the bone marrow-containing micronucleus polychromatic erythrocyte (PCE) rate of female and male mice in the three dose groups of Compound 2 was not significantly different (P>0.05). The micronucleus rate of the positive control compared with that of the test group and the negative control (P<0.01), the difference was statistically significant. There was no obvious gender difference in micronucleus between male and female in the same dose group of the test article. The results show that the micronucleus results of the mouse bone marrow cells treated with Compound 2 are negative, and it can be considered that Compound 2 does not have genotoxicity under these test conditions.

TABLE 9

Micronucleus test results of Compound 2 in bone marrow cells of female mice ($n = 5, \bar{x} \pm SD$)

| Groups | Dose (mg/kg) | Number of animals | PCE Micronucleus rate (‰) | P value 1 | P value 2 |
|---|---|---|---|---|---|
| High | 500 | 5 | 2.77 ± 1.06 | 0.01** | 0.03* |
| Medium | 250 | 5 | 2.36 ± 1.33 | 0.01** | 0.18 |
| Low | 125 | 5 | 0.79 ± 1.09 | 0.00** | 0.99 |
| Normal saline | — | 5 | 0.78 ± 1.07 | — | |
| Positive control | 40 mg/kg | 5 | 15.00 ± 2.42 | | — |

Note:
*Comparison of each test group with the negative control, P > 0.05,
**Comparison of each test group with the positive control, P < 0.01.

TABLE 10

Micronucleus test results of Compound 2 in bone marrow cells of male mice ($n = 5, \bar{x} \pm SD$)

| Groups | Dose (mg/kg) | Number of animals | PCE micronucleus rate (‰) | P value 1 | P value 2 |
|---|---|---|---|---|---|
| High | 500 | 5 | 2.74 ± 1.06 | 0.02* | 0.03* |
| Medium | 250 | 5 | 2.07 ± 0.88 | 0.00** | 0.07 |
| Low | 125 | 5 | 0.79 ± 1.08 | 0.00** | 0.99 |
| Normal saline | — | 5 | 0.78 ± 1.07 | — | |
| Positive control | 40 mg/kg | 5 | 15.20 ± 2.37 | | — |

Note:
*Comparison of each test group with the negative control, P > 0.05,
**Comparison of each test group with the positive control, P < 0.01.

Example 4.4 Sperm Abnormality Test of Compound 2 in Mice

1 Materials and Methods 1.1 Experimental Materials

Experimental animals: 60 clean-grade healthy male ICR mice having the average weight of 18-20 g, purchased from the Comparative Medicine Center of Yangzhou University.

Reagents: Test agent, Compound 2, provided by Guangzhou Insighter Biotechnology Co., Ltd., was prepared into a suspension of the required concentration with 1.0% sodium carboxymethyl cellulose before use; the mutagenic positive control article of cyclophosphamide with the content of 99.00%; other reagents include sodium chloride, methanol, and eosin, all of analytical grade; self-prepared physiological saline; self-prepared eosin aqueous solution (2%).

Instruments: Biological microscope (with filter and 100× objective lens), cell counter, and the like.

1.2 Procedures

Dose grouping and test article solution preparation: $LD_{50}$ of administration of toxicant by oral of Compound 2 is 1000 mg/kg, according to Compound 2's $LD_{50}$ and its physical and chemical properties, 500 mg/kg body weight (high), 250 mg/kg body weight (medium), and 125 mg/kg body weight (low) test groups were set. The test article, Compound 2 was diluted with 1.0% sodium carboxymethyl cellulose as a solvent, and it was given by oral in different concentrations and the same volume. There is also a positive control and a negative (solvent) control. The cyclophosphamide was selected as the positive control (40 mg/kg).

Grouping of experimental animals: 60 healthy male mice were individually weighed, labeled and numbered, and they were divided into 5 groups with 12 mice in each group using a completely random method. It was ensured that 10 animals in each group survive for sampling and film making after administration.

Administration: The administration method is carried out according to GB15193.7-2003. The test group, the negative control and the positive control are all given the test article by oral once a day for 5 consecutive days. The weight of the mouse for each administration was weighed, and the volume of the test article that each mouse should administer was calculated according to the requirements of the mouse 0.2 mL/10 g b.w.

Sampling and sample preparation: The mice were sacrificed by cervical dislocation on the Day 35 after the first administration, and sampling and film making were performed. 10 mice were sampled in each dose group. The abdominal cavity was cut, the epididymis on both sides were separated and extracted, and put in a petri dish containing 2 mL of normal saline; The mice were longitudinally cut with ophthalmological scissors for 2 times, the normal saline in it was pipetted with a straw for several times, and let stand for 3 min; the tissue fragments were filtered with a 4-layer of lens cleaning paper, 1 drop of the filtrate was drawn onto the glass slide, the slide was pushed with 4 slides per mouse; the slide in the air dried naturally, and fixed with methanol for 10 minutes, and dried; stained with 2% eosin for 1 h, the dye solution was gently washed off with water, and it was dried naturally before microscopic examination.

Data collation and analysis: The number of normal sperm, the number of abnormal sperm and the number of various types of abnormal sperm were read and counted in each dose group of mice. The sperm abnormality rate (%) of mice in each dose group and the percentage (%) of various types of abnormal sperm were calculated, and the standard deviation of the sperm abnormality rate of mice was also calculated in each dose group. Calculation as follows:

$$\text{Sperm abnormality rate } (\%) = \frac{\text{The number of abnormal sperm}}{\text{The number of normal sperm and abnormal sperm}} \times 100\%$$

The sperm abnormality rate of mice in each dose group was statistically compared with the sperm abnormality rate of mice in the negative (solvent) control. The experimental data was processed by SPSS 11.0 statistical software, and the analysis results were expressed as $\bar{x}\pm SD$, and the incidence of sperm abnormalities was statistically processed according to the $X^2$ ($\alpha=0.05$).

Results judgment: The results of the positive control and the negative control were firstly observed. It is required that the abnormal sperm rate of the negative control should be within the quality control range (usually 0.8%-3.4%), and the abnormal sperm rate of the positive control group is significantly different from that of the negative control ($P<0.01$). When the sperm abnormality rate of the mice in the test group is twice or more than that of the negative control, or there is a statistically significant difference, and there is a dose-reverse relationship, the result can be repeated, and the result can be judged to be positive, that is the test agent is a sperm abnormality mutagen. If the dose of the test group has caused the animal to die, while the sperm abnormality has not increased, the result can be judged to be negative.

2 Results

The results of the mice sperm abnormality test of Compound 2 are shown in Table 11. It can be seen from the table that after statistical processing, there is no significant difference between the sperm abnormality rate of the three dose groups of Compound 2 and the negative control ($P>0.05$), while the positive control was compared with the three dose groups and the negative control, the difference was statistically significant ($P<0.01$), and the difference was significant. The results show that the sperm abnormality results of the mice treated with Compound 2 are negative, and it can be judged that Compound 2 does not have reproductive genetic toxicity.

1.2 Test Agents and Reagents

Test agent: Compound 2, batch number: 20150713, was provided by Guangzhou Insighter Biotechnology Co., Ltd.

Other reagents: Formaldehyde, glacial acetic acid, 2,4,6-trinitrophenol, potassium hydroxide, glycerin, alizarin red, sodium pentobarbital, alizarin red stock solution (glacial acetic acid 5.0 mL, glycerol 10 mL, 1% chloral hydrate 60.0 mL to make a mixed solution, an appropriate amount of Alizarin Red was taken while stirring until it is saturated, and stored in a brown bottle), Alizarin Red application solution (1 mL of Alizarin Red stock solution was taken and 1% potassium hydroxide solution was introduced to dilute the mixture to 1000 mL and placed in a brown bottle. Freshly prepared before use), clear solution A (200 mL of glycerin and 10 g of potassium hydroxide were mixed and diluted to 1000 mL with distilled water), clear solution B (glycerin and distilled water were mixed in equal amounts), Fixed liquid Bouins solution (mixed with 75 volumes of 2,4,6-trinitrophenol (picric acid) saturated solution, 20 volumes of formaldehyde, and 5 volumes of glacial acetic acid).

1.3 Instruments

Biological microscopes and stereo microscopes, vernier calipers (centimeters), and other commonly used laboratory equipment.

1.4 Dosage Group Design

The 64 pregnant Wistar rats were divided into 4 groups, 16 rats in each group were tested. 30 mg/kg body weight (high), 8 mg/kg body weight (medium), 2 mg/kg body weight (low) were set as three dose groups, and also a negative (solvent) control was set up.

1.5 Treatment of Sample and Administration

The test agent, Compound 2 was prepared as a suspension of the required concentration with 0.5% sodium carboxymethyl cellulose, and the test Wistar rats were administered by oral in a volume of 1 mL/100 g body weight.

1.6 Procedures

The test operation is carried out in accordance with GB15193.14-2015 "Teratogenicity Test".

TABLE 11

The effects of Compound 2 on the incidence of sperm abnormality in mice (n = 10, $\bar{x}$ ± SD)

| Groups | | Number of animals | Total number of checked sperm | Types of abnormal sperm: No hook | Banana shape | Amorphous | Fat head | Fold tail | Double head | Double tail | Total number of abnormal sperm | Number of Abnormal sperm ($\bar{x}$ ± SD) | Sperm deformity (%) |
|---|---|---|---|---|---|---|---|---|---|---|---|---|---|
| IST-7003 | high* | 10 | 10000 | 63 | 22 | 106 | 10 | 9 | 5 | 9 | 224 | 22.40 ± 1.84* | 2.17 ± 0.16 |
| (Isoprofen) | medium* | 10 | 10000 | 65 | 21 | 111 | 7 | 5 | 5 | 7 | 221 | 22.10 ± 1.37* | 2.14 ± 0.14 |
| | low* | 10 | 10000 | 69 | 16 | 118 | 5 | 5 | 4 | 6 | 223 | 22.30 ± 1.70* | 2.15 ± 0.16 |
| Negative control* | | 10 | 10000 | 67 | 21 | 113 | 8 | 5 | 5 | 6 | 225 | 22.50 ± 1.35 | 2.18 ± 0.13 |
| Positive control* | | 10 | 10000 | 149 | 91 | 248 | 21 | 12 | 13 | 25 | 559 | 55.90 ± 2.08** | 5.26 ± 0.18 |

Note:
*Comparison of each test group with the negative control $P > 0.05$,
**Comparison of each test group with the positive control $P < 0.01$

Example 4.5 Teratogenicity Test of Compound 2 in Rats

1 Materials and Methods 1.1 Experimental Animal

Wistar rats with the weight of 220-250 g, were purchased from the Comparative Medicine Center of Yangzhou University.

Dosage regimen: Oral administration is adopted. From the Day 6 to the Day 15 after ingravidation, the test article was administered once a day for 10 consecutive days. The pregnant rats were weighed on the Day 0, 7, 12, 16 and 20 after ingravidation.

Clinical observation: The food intake, drinking water and weight gain of pregnant rats were checked and recorded during the experiment, and the general behavior, poisoning and death of pregnant rats were observed.

Execution, inspection and recording of pregnant mice: The pregnant mice were weighed on the Day 20 of pregnancy, and 0.6-0.8 mL of 2% sodium pentobarbital solution was injected into the intraperitoneal cavity of every mouse, and then the pregnant mice after anesthesia were executed. The ovaries and uterus were taken out by caesarean section. These parameters were further checked including the number of corpus luteum, absorbed fetuses, stillbirths, live fetuses, the ratio of female to male live fetuses, the weight of the uterus connected to the fetus, the weight of the uterus, and the like.

Inspection and recording items of live fetus: The weight, body length, and tail length of the live fetus were measured, and the appearance of the live fetus for abnormalities was checked. Fetal mouse body surface examination parts include head, trunk and limbs. Head examination items include anencephaly, encephalocele, parietal cleft, hydrocephalus, microcephaly, facial cleft, microphthalmia, exophthalmos, and no ears symptoms, microtia, low ears, jawlessness, gnatism, cleft jaw, and cleft lip. Trunk examination items include sternal cleft, thoracic cleft, spinal bifida, abdominal cleft, scoliosis, kyphosis, umbilical hernia, hypospadias, no anus, short tail, curled tail, and no tail. Examination items for limbs include multiple limbs, no limbs, short limbs, half limbs, polytoes, no toes, double toes, short toes, and missing toes.

Inspection and recording items of fetal bone: Fetal bone specimens from half of the live fetus in each litter were prepared; the fetal specimens were placed in a small plate; the overall observation was performed under a stereoscopic microscope by a transmission light source, and then the bones were gradually inspected. The inspection parts and items include occipital bone (absence of ossification center), spinal bone (number, abnormal shape, fusion, longitudinal fissure, partial dehiscence, loss of ossification center, narrowing, detachment), pelvic bone (missing ossification center, abnormal shape, Fusion, dehiscence, narrowing, detachment), limb bones (abnormal number and shape), carpal bones (absence of ossification center), metacarpal bones (abnormal shape), phalanx (abnormal shape), ribs (abnormal number, shape, fusion, classification Fork, defect) and sternum (number, fusion, loss of ossification center).

Inspection and recording items of fetal visceral: The other half of the live fetus in each litter were put into the fixative, and visceral inspection was performed after two weeks of fixation. The inspection sites include the head (spine cord), chest and abdomen. Head examination items include hypoplasia of the olfactory bulb, dilatation of the lateral ventricle, dilatation of the third ventricle, anencephaly, aneurysm, microphthalmia, corneal defect and monocular. Chest examination items include right heart, atrial septal defect, ventricular septal defect, aortic arch, esophageal atresia, tracheal stenosis, apulmonary syndrome, polypulmonary disease, pulmonary fusion, septal hernia, tracheoesophageal basket and ectopic internal organs. Abdominal examination items include abnormal liver lobes, absent adrenal glands, polycystic kidney, horseshoe kidney, absent bladder, absent testis, absence of ovaries, ectopic ovaries, absence of uterus, hypoplasia of uterus, hydronephrosis, absence of kidneys and hydrosalpinx.

1.7 Data Analysis

The statistics of various rates was tested by X2; the weight gain of pregnant mice is analyzed by variance; the length, weight, average number of live births, and the weight of consecutive fetuses of fetal mice are tested by t.

2 Results and Discussion 1.1 the Effect of the Test Article on the General Behavior, Poisoning and Death of Pregnant Rats.

During the experiment, there was no abnormality in the feeding and drinking of the pregnant rats in each dose group of the test article, and no poisoning or death occurred.

2.2 the Effect of the Test Article on the Weight of Pregnant Mice

The effects of the test article on the normal food, drinking, and weight gain of pregnant rats are shown in Table 12. The software statistical analysis showed that, the net weight gain of pregnant rats was lower than that of the control (P<0.05) except for the high-dose group, and there was no significant difference in the weight gain of pregnant rats among the other groups (P>0.05).

TABLE 12

The effects of Compound 2 on the daily gain of pregnant rats ($\bar{x} \pm SD$)

| Groups | Number of pregnant rats | Weight gain of pregnant rats (g/rat/day) Day 0-7 | Day 7-12 | Day 12-16 | Day 16-20 | Net weight gain (g/rat) |
|---|---|---|---|---|---|---|
| High | 16 | 2.05 ± 2.62 | 1.07 ± 1.35 | 2.17 ± 2.37 | 0.00 ± 0.00 | 28.33 ± 18.65* |
| Medium | 16 | 2.46 ± 0.63 | 2.63 ± 1.15 | 3.08 ± 1.82 | 9.40 ± 2.18 | 80.33 ± 14.16 |
| Low | 16 | −1.26 ± 8.26 | 5.57 ± 11.83 | 7.13 ± 3.39 | 4.65 ± 1.25 | 66.08 ± 22.52 |
| Negative control | 16 | 1.93 ± 0.52 | 2.95 ± 1.06 | 3.46 ± 2.29 | 10.94 ± 2.53 | 85.83 ± 10.65 |

Note:
*Comparison with negative control, P < 0.05.

2.3 the Effect of the Test Article on the Reproductive Function of Rats

The effects of the test article on the reproductive function of rats are shown in Table 13. Compared with the negative control, the average number of live births, absorbed births and still births in each dose group of the test article were not significantly different (P>0.05).

TABLE 13

The effect of Compound 2 on the reproductive function of rats ($\bar{x} \pm SD$)

| Groups | Number of pregnant rats | Average number of corpus luteum | Average number of stillbirths | Average number of absorbed fetuses | Average number of implants |
|---|---|---|---|---|---|
| High | 16 | 8.55 ± 1.86 | 0.00 ± 0.00 | 0.27 ± 0.47 | 8.55 ± 1.86 |
| Medium | 16 | 8.17 ± 1.95 | 0.17 ± 0.58 | 0.00 ± 0.00 | 8.17 ± 1.95 |
| Low | 16 | 8.40 ± 1.96 | 0.00 ± 0.00 | 0.10 ± 0.32 | 8.40 ± 1.96 |
| Negative control | 16 | 8.58 ± 1.51 | 0.08 ± 0.29 | 0.17 ± 0.39 | 8.58 ± 1.51 |

2.4 Embryonic Toxicity of Test Article to Rats

The Effects of Test Articles on Rat Embryos were Shown in Table 14 and Table 15. Compared with the negative control, the implantation rate, absorbed fetal rate, stillbirth rate, live fetal rate, and male-to-female ratio in each dose group of the test article were not significantly different (P>0.05); the uterine weight, placental weight, live fetal weight, body length and tail length were also not significantly different from those of the control (P>0.05).

TABLE 14

Embryonic toxicity of Compound 2 to rats (I)

| Groups | Number of pregnant rats | Implantation rate (%) | Absorbed fetuses (%) | Stillbirth rate (%) | Live birth rate (%) | Male to female ratio |
|---|---|---|---|---|---|---|
| High | 16 | 100.00 | 2.13 | 0.00 | 97.87 | 0.97 |
| Medium | 16 | 100.00 | 0.00 | 2.00 | 98 | 0.84 |
| Low | 16 | 100.00 | 1.19 | 0.00 | 98.81 | 0.88 |
| Negative control | 16 | 100.00 | 1.94 | 0.97 | 97.09 | 0.86 |

TABLE 15

Embryonic toxicity of compound 2 to rats (II) ($\bar{x} \pm SD$)

| Groups | Number of pregnant rats | Number of live births | Average weight of uterine and fetal (g) | Average uterine weight (g) | Average fetal weight (g) | Average fetal mouse weight (g) | Average body length of fetal mouse (cm) | Average tail length of fetal mouse (cm) |
|---|---|---|---|---|---|---|---|---|
| High | 16 | 123 | 49.97 ± 11.07 | 4.61 ± 0.80 | 6.69 ± 1.35 | 3.43 ± 0.37 | 3.56 ± 0.23 | 1.37 ± 0.12 |
| Medium | 16 | 127 | 44.38 ± 10.39 | 4.14 ± 1.40 | 5.44 ± 1.91 | 3.29 ± 0.41 | 3.51 ± 0.23 | 1.25 ± 0.12 |
| Low | 16 | 112 | 48.08 ± 11.15 | 3.75 ± 1.51 | 6.46 ± 1.87 | 3.33 ± 0.33 | 3.55 ± 0.23 | 1.22 ± 0.10 |
| Negative control | 16 | 135 | 52.65 ± 8.56 | 4.01 ± 0.81 | 7.09 ± 1.00 | 3.78 ± 0.33 | 3.65 ± 0.15 | 1.38 ± 0.11 |

2.5 Teratogenicity of Test Article on Fetal Mice

The effects of the test articles on the appearance of fetal mice, bone development, and internal organ development are shown in Table 16. Compared with the negative control group, the incidence of appearance abnormalities in each dose group had no significant difference (P>0.05). In terms of skeletal development, fetal mice in each dose group showed no abnormalities in the examination of the parietal bones, sternum, ribs, and spine bones. In terms of visceral development, the fixed biopsy of the fetal rat's internal organs showed that there was no abnormality in the fetal rats in each dose group of the test article. There was no significant difference in the visceral observation indexes of each dose group compared with the negative control.

TABLE 16

Teratogenic effects of Compound 2 on rats

| Groups | Number of pregnant rats | Number of live births | Appearance abnormality Teratogenicity (%) | Appearance abnormality Maternal abnormality rate (%) | Skeletal abnormality Teratogenicity (%) | Skeletal abnormality Maternal abnormality rate (%) | Visceral abnormality Teratogenicity (%) | Visceral abnormality Maternal abnormality rate (%) |
|---|---|---|---|---|---|---|---|---|
| High | 16 | 123 | 0.00 | 0.00 | 0.00 | 0.00 | 0.00 | 0.00 |
| Medium | 16 | 127 | 0.00 | 0.00 | 0.00 | 0.00 | 0.00 | 0.00 |
| Low | 16 | 112 | 0.00 | 0.00 | 0.00 | 0.00 | 0.00 | 0.00 |
| Negative control | 16 | 135 | 0.00 | 0.00 | 0.00 | 0.00 | 0.00 | 0.00 |

3. Conclusions

The above results indicate that the net weight gain of pregnant rats in the high-dose compound 2 group was lower than that in the control ($P<0.05$), while the weight gain of pregnant rats in the other dose groups was normal. The principle of dose group design in GB15193.14-2015 "Teratogenicity Test" is that for the test article that can obtain $LD_{50}$, each dose group can set the dose of each group according to $LD_{50}$, and in principle, high doses should make some pregnant mice appear toxic effects, such as weight loss. There was no significant difference in the average number of live fetuses, absorbed fetuses and stillbirths in each dose group of compound 2 compared with the negative control ($P>0.05$); There was no significant difference in the average weight, body length and tail length of live fetuses in each dose group compared with the negative control ($P>0.05$). Compared with the negative control, there was no significant difference in the incidence of appearance abnormalities in each dose group of compound 2 ($P>0.05$); no abnormal development was found in the bone examination of the fetus, and no abnormality or abnormality was found in the internal organ examination.

In summary, under the conditions of this experiment, high-dose compound 2 has slight maternal toxicity to rats, and Compound 2 has not been found to have embryo toxicity and teratogenic effects on rats.

What is claimed is:

1. A process for managing, treating or alleviating a disease caused by bacterial infection in an animal by administering to the animal a therapeutically effective amount of a diaminoguanidine derivative of Formula (I), or a stereoisomer, geometric isomer, tautomer, solvate, pharmaceutically acceptable salt, or prodrug thereof:

Formula (I)

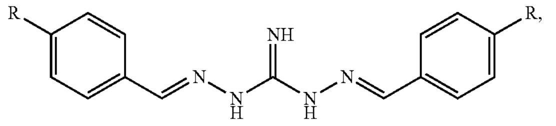

wherein,

R is according to Formula (II) or (III):

Formula (II)

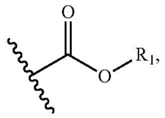

or

Formula (III)

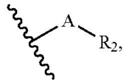

wherein $R_1$ is a linear or branched $C_1$-$C_{20}$ alkyl group; A is O, NH or S; and $R_2$ is a linear or branched $C_3$-$C_{14}$ alkyl group, $C_5$-$C_6$ cycloalkyl, $C_6$ aryl, or $—CH_2(C_6$ aryl); and wherein the pharmaceutically acceptable salt is a D,L-lactic acid salt, methanesulfonic acid salt, 2-hydroxyethyl sulfonic acid salt, citric acid salt, tartaric acid salt, benzoic acid salt, succinic acid salt, fumaric acid salt, maleic acid salt, acetic acid salt, sulfuric acid salt, phosphoric acid salt, or oxalic acid salt, and wherein the bacterial infection is caused by *Staphylococcus aureus*, and wherein the disease is mastitis, a skin infection, a gastrointestinal infection, a respiratory infection, or a genitourinary system disease.

2. The process of claim 1, wherein R is according to Formula (II), and $R_1$ is a linear $C_1$-$C_{20}$ alkyl group.

3. The process of claim 2, wherein $R_1$ is a linear $C_1$-$C_{12}$ alkyl group.

4. The process of claim 3, wherein $R_1$ is methyl.

5. The process of claim 1, wherein R is according to Formula (III), and A is O.

6. The process of claim 1, wherein R is according to Formula (III), and A is NH.

7. The process of claim 1, wherein R is according to Formula (III), and $R_2$ is a linear $C_3$-$C_{14}$ alkyl group.

8. The process of claim 1, wherein R is according to Formula (III), and $R_2$ is a branched $C_3$-$C_{14}$ alkyl group.

9. The process of claim 8, wherein $R_2$ is a branched $C_3$ alkyl group, or a branched $C_4$ alkyl group; and A is O.

10. The process of claim 1, wherein the disease is endometritis, mastitis, and/or skin infection.

11. The process of claim 1, wherein the diaminoguanidine derivative is a D,L-lactic acid salt, methanesulfonic acid salt, 2-hydroxyethyl sulfonic acid salt, citric acid salt, tartaric acid salt, benzoic acid salt, succinic acid salt, fumaric acid salt, maleic acid salt, acetic acid salt, sulfuric acid salt, phosphoric acid salt, or oxalic acid salt.

* * * * *